United States Patent [19]

Reinitz

[11] 4,192,955
[45] Mar. 11, 1980

[54] PROCESS FOR THE RECOVERY OF 2,2-BIS(4-HYDROXYPHENYL) PROPANE

[75] Inventor: Clayton W. Reinitz, Mt Vernon, Ind.

[73] Assignee: General Electric Company, Pittsfield, Mass.

[21] Appl. No.: 865,297

[22] Filed: Dec. 18, 1977

[51] Int. Cl.$^2$ .................... C07C 37/44; C07C 37/24
[52] U.S. Cl. .................................. 568/724; 568/728
[58] Field of Search ............................. 568/724, 728

[56] References Cited

U.S. PATENT DOCUMENTS

| | | | |
|---|---|---|---|
| 2,845,464 | 7/1958 | Lutin | 568/724 |
| 2,959,622 | 11/1960 | Gumme et al. | 568/724 |
| 3,111,544 | 11/1963 | Jons et al | 568/724 |
| 3,162,690 | 12/1964 | Marx et al. | 568/724 |
| 3,359,281 | 12/1967 | Schlichting et al. | 568/724 |
| 3,627,846 | 12/1971 | Meyer | 568/724 |
| 3,919,330 | 11/1975 | Kwantes et al. | 260/619 A |
| 3,936,507 | 2/1976 | Ligorati et al. | 568/724 |
| 3,972,950 | 8/1976 | Kwantes | 260/619 A |

FOREIGN PATENT DOCUMENTS 902350  8/1960  United Kingdom .................... 568/724

Primary Examiner—Norman Morgenstern
Attorney, Agent, or Firm—Morgan, Finnegan, Pine, Foley & Lee

[57] ABSTRACT

2,2-Bis(4-hydroxyphenyl) propane, herein referred to as bisphenol-A, is recovered from crude or partially purified adducts with phenol by dissolving in a solvent in which the bisphenol-A phenol adduct is soluble and which is miscible with water, mixing the resulting adduct-solvent solution with water at a temperature at which the adduct is soluble therein, cooling the mixture to a temperature where substantially all of the bisphenol-A precipitates substantially without co-precipitation of the phenol, and physically recovering said precipitated bisphenol-A. Also contemplated is an embodiment wherein such a solvent solution of bisphenol-A or the adduct thereof with phenol is added to the water, rather than vice-versa, and high purity, easy to handle rhombic crystals of bis-phenol-A are produced.

11 Claims, No Drawings

PROCESS FOR THE RECOVERY OF 2,2-BIS(4-HYDROXYPHENYL) PROPANE

This invention is directed to a process employing a solvent and water to recover 2,2-bis(4-hydroxyphenyl) propane from crude, impure and partially purified mixtures containing the same or an adduct thereof with phenol.

BACKGROUND OF THE INVENTION

The use of high purity 2,2-bis(4-hydroxyphenyl) propane, herein referred to as bisphenol-A, as a reactant in the preparation of subsequent formulations such as the preparation of polycarbonate resins is well known in the art. One method of producing biphenol-A is that of reacting acetone with phenol in the presence of an acid catalyst such as hydrochloric acid. In such a reaction, two moles of phenol react with one mole of acetone to produce one mole of bisphenol-A and the water of reaction and acid catalyst are then distilled off to thus produce a completed reaction mixture. In those cases when the completed reaction mixture has phenol in sufficient excess over the initial two-mole reaction requirement or when additional phenol is added to yield a completed reaction mixture wherein phenol is present in at least a ratio of one mole phenol to one mole bisphenol-A, an equimolar adduct of bisphenol-A and phenol will form upon cooling said completed reaction mixture to about 40° C. An improved method of recovering the bisphenol-A from reaction mixtures containing it or an adduct thereof is the subject of the instant invention.

In U.S. Pat. Nos. 3,919,330 and 3,972,950, methods for recovering bisphenol-A from impure mixtures are described. The method with which the patents deal involves dissolving the crude bisphenol-A in a polyhydroxy compound, e.g., ethylene glycol, then adding a certain amount of water, whereby the desired material is precipitated in pure form and finally recovered. These patents each state that East German Patent specification 53,374 crystallizes bisphenol-A from a methanol solution by the addition of water or by the addition of halohydrocarbons, preferably dichloroethane, plus water, followed by washing the crystals. Chemical Abstracts, entry 66, 38331 j (1967) describes another procedure in which bisphenol-A is heated under a vacuum to remove free phenol, then dissolved in methanol, treated with activated carbon, filtered and finally water is added to the filtrate to give purified bisphenol-A. The U.S. patents and the abstract are incorporated herein by reference.

It is noteworthy that in none of the cases was the bisphenol-A in the form of an equimolar adduct with phenol and in all of the cases the water was added to the solution of crude bisphenol-A instead of vice-versa. It has now been surprisingly discovered that the adduct can be broken and the bisphenol-A can be readily obtained in higher than expected purity, regardless of the order of contacting the solution with water and, as a second discovery, that the addition of the solution of either bisphenol-A or the adduct to water provides highly pure bisphenol-A in the form of easily handled rhombic crystals.

DESCRIPTION OF THE INVENTION

According to the present invention, 2,2-bis(4-hydroxyphenyl) propane, herein referred to as bisphenol-A, is recovered from an equimolar adduct of bisphenol-A and phenol by a process comprising dissolving the adduct in a solvent in which the adduct is soluble and which is miscible with water, mixing the resulting adduct-solvent solution with water at a temperature at which the adduct is soluble therein, cooling the resulting mixture to a temperature where substantially all of the bisphenol-A precipitates substantially without coprecipitation of the phenol, and physically recovering the precipitated bisphenol-A. In another aspect, the present invention provides a process comprising dissolving the impure mixture in a solvent in which (i) that is 2,2-bis-(4-hydroxyphenyl) propane or (ii) that is an equimolar adduct of 2,2-bis(4-hydroxyphenyl) propane and phenol is soluble and which is miscible with water, adding the resulting solution of (i) or (ii) in said solvent to water at a temperature at which (i) or (ii) is soluble therein, cooling the resulting mixture to a temperature where substantially all of the 2,2-bis(4-hydroxyphenyl) propane precipitates and physically recovering said precipitated 2,2-bis(4-hydroxyphenyl) propane.

The crude starting materials are obtained, e.g., as described above and, more particularly, as shown in the above-referenced patents.

The equimolar adduct of bisphenol-A and phenol can be obtained by simply cooling the completed reaction mixture wherein bisphenol-A is produced in the reaction of phenol and acetone as earlier discussed. A bisphenol-A/phenol adduct can also be obtained by mixing at least equal moles of bisphenol-A of any quality and phenol, heating the mixture to form a solution, and cooling the solution to form the adduct.

The solvent in which the bisphenol-A starting materials are dissolved can be at room temperature or low heat, with the concentration by weight of adduct to solvent being from about 5% to saturation. Representative but not limiting examples of solvents in which the adduct is soluble and which are miscible with water include lower alkyl alcohols such as methyl, ethyl, n-propyl, iso-propyl, isobutyl, and tert-butyl; lower alkyl ketones such as acetone and methyl ethyl ketone; lower alkyl nitriles, such as acetonitrile; ethers such as tetrahydrofuran and p-dioxane; lower alkanoic acids, such as formic, acetic and propionic; and the like.

The resulting solutions in the solvent are mixed with water having a preferred temperature of from about 45° C. to about 100° C. and at a preferable ratio of one part by weight of bisphenol-A or adduct to from 1 to about 10 parts by weight of water. The resulting mixture is stirred and cooled to a temperature where substantially all of the bisphenol-A precipitates, substantially without coprecipitation of the phenol in cases where the adduct is employed. A preferred temperature range for said bisphenol-A precipitation is from about 25° C. to about 50° C. If a bisphenol-A/phenol adduct rather than a crude bisphenol-A is employed as the starting material from which bisphenol-A is recovered, the phenol from the adduct will remain in solution and in contact with the bisphenol-A thus precipitated. This phenol appears to act as a wash to the precipitated bisphenol-A to thereby yield bisphenol-A having fewer impurities than that obtained when a crude bisphenol-A not having an equal mole of phenol present is the starting material.

The bisphenol-A thus isolated from the original starting material can be physically recovered from its mother liquor as by filtration or centrifugation, and can be further purified if desired as with a water and/or solvent wash. The process in which the solution is added to water produces crystals in the form of rhomboids, rather than long needles, the rhomboids having a smaller length to diameter ratio and therefore being less fragile and easier to handle.

DESCRIPTION OF THE PREFERRED EMBODIMENTS

The following examples are set forth to illustrate more clearly the principle and practice of this invention to those skilled in the art. Unless otherwise specified, where parts or percents are mentioned, they are parts or percents by weight. The adducts employed in the respective examples are first washed with 0.5 parts by weight phenol per part by weight of adduct.

EXAMPLE 1

One hundred grams of an essentially equimolar adduct of bisphenol-A and phenol is dissolved at room temperature in 200 grams of methanol. This solution is added to 800 grams of water at a temperature of 50° C. and is stirred to produce a mixture. The resulting mixture is allowed to cool to 40° C. to permit isolation of bisphenol-A as a crystalline precipitate substantially without co-precipitation of phenol. Separation of the precipitate from the mother liquor is performed by vacuum filtration to thereby yield bisphenol-A.

EXAMPLE 2

Twenty grams of the adduct of Example 1 is dissolved at room temperature in 20 ml of ethanol. The resulting solution is added to 400 ml of water at a temperature of 50° C. and is stirred to produce a mixture. Cooling this mixture to 40° C. results in isolation of bisphenol-A as a crystalline precipitate substantially without co-precipitation of phenol. The bisphenol-A is recovered by vacuum filtration.

EXAMPLE 3

In the same manner as Example 2, 20 grams of adduct is dissolved in 20 ml of acetonitrile. The resulting solution is added to 400 ml of water at a temperature of 50° C. and stirred to produce a mixture. Cooling this mixture to 40° C. results in crystallization of bisphenol-A.

EXAMPLE 4

In the same manner as in Example 2, 25 grams of adduct is dissolved in 35 ml of tetrahydrofuran. This solution is added to 1,450 ml of water at a temperature of 50° C. and stirred to produce a mixture. Cooling this mixture to 40° C. results in crystallization of bisphenol-A.

EXAMPLE 5

In the same manner as in Example 2, 25 grams of adduct is dissolved in 35 ml of acetone. This solution is added to 700 ml of water at a temperature of 50° C. and stirred to produce a mixture. Cooling this mixture to 40° C. results in precipitation of bisphenol-A.

EXAMPLE 6

Fifteen grams of crude bisphenol-A containing 0.014% phenol and 0.62% total known impurities (less phenol) are dissolved in 23 ml of methanol. This solution is added to 184 ml of water at a temperature of 50° C., stirred, and cooled to 40° C. The crystalline bisphenol-A is separated by centrifugation, washed with 92 ml of 50° C. water and placed in a 50° C. vacuum oven for one hour. Results of liquid chromatographic analysis is shown in the Table hereafter.

EXAMPLE 7

This Example simulates the phenol quantity present when a phenol/bisphenol-A adduct solution is added to the water from which crystalline bisphenol-A is recovered. Example 6 is repeated exactly except that 6.2 grams of phenol (a molar equivalent of bisphenol-A) is also added to the methanol. Results of liquid chromatographic analysis are shown below in the Table.

Table

| Analysis of Impurities Present in Final Bisphenol-A Product | | |
|---|---|---|
| | Wt.% Phenol | Total Wt.% Known Impurities (Less Phenol) |
| Control (Starting bisphenol-A) | 0.014 | 0.62 |
| Bisphenol-A from Example 6 | NDA* | 0.44 |
| Bisphenol-A from Example 7 | 0.15 | 0.21 |

*NDA = No Detectable Amount

As is evident from the Table, the presence of phenol in an amount equal to the molar equivalent of bisphenol-A, as is present from the phenol/bisphenol-A adduct, reduces by more than 50% the total weight of known impurities, excluding phenol, present in the bisphenol-A final product as compared to the bisphenol-A final product when a molar equivalent of phenol is not present. Thus, using an adduct in the process of the instant invention produces bisphenol-A having fewer impurities than those present if bis-phenol-A not in the form of an adduct is used.

EXAMPLE 8

12,000 g of water is placed in a suitable-sized reaction kettle and there is slowly added thereto a solution of 6000 g of partially purified bisphenol-A dissolved in 6000 g of methanol. The mixture was agitated slowly for 1 hour after addition was complete, during which time the product precipitated in the form of rhombic crystals. The crystals were isolated by centrifuging in a Tolhurst basket centrifuge, washed with 0.5 parts of water per part of bisphenol-A wetcake, and recovered. The first crop of separated solids weighs 5336.5 g, an 88.94% recovery of pure material. A second crop is obtained by adding 1 liter of water to the mother liquor. This weighs 195.4 g., 3.26% recovery.

Obviously, other modifications and variations of the present invention are possible in light of the above teachings. It is, therefore, to be understood that changes may be made in the particular embodiments of the invention described which are within the full intended scope of the invention as defined by the appended claims.

I claim:

1. A process to recover 2,2-bis(4-hydroxyphenyl) propane from an equimolar adduct of 2,2-bis(4-hydroxyphenyl) propane and phenol, the process comprising dissolving the adduct in a solvent in which the adduct is soluble and which is miscible with water, mixing the resulting adduct-solvent solution with water at a temperature at which the adduct is soluble therein, cooling the resulting mixture to a temperature where substantially all of the 2,2-bis(4-hydroxyphenyl) propane precipitates substantially without co-precipitation of the phenol and physically recovering said precipitated 2,2-bis(4-hydroxyphenyl) propane.

2. A process as defined in claim 1 wherein the solvent is a lower alkyl alcohol, a lower alkyl ketone, a lower alkyl nitrile, a lower alkanoic acid, tetrahydrofuran or dioxane.

3. A process as defined in claim 2 wherein the solvent is a lower alkyl alcohol.

4. A process as defined in claim 3 wherein the alcohol is methanol or ethanol.

5. A process as defined in claim 2 wherein the solvent is acetonitrile.

6. A process as defined in claim 2 wherein the solvent is tetrahydrofuran.

7. A process as defined in claim 2 wherein the solvent is acetone.

8. A process as defined in claim 1 wherein the concentration of adduct to solvent is from about 5% to saturation.

9. A process as defined in claim 1 wherein the quantity of water with which the adduct-solvent solution is mixed is from 1 to about 10 times the weight of the adduct.

10. A process as defined in claim 1 wherein the temperature of the water with which the adduct-solvent solution is mixed is from about 45° C. to about 100° C.

11. A process as defined in claim 1 wherein the temperature to which the mixture of adduct, solvent and water is cooled for precipitation of 2,2-bis(4-hydroxyphenyl) propane is from about 25° C. to about 50° C.

* * * * *